United States Patent [19]

Poetsch et al.

[11] Patent Number: 5,496,499

[45] Date of Patent: Mar. 5, 1996

[54] BIPHENYLETHANES AND LIQUID-CRYSTALLINE PHASE

[75] Inventors: Eike Poetsch, Mühltal; Volker Meyer, Gross-Zimmern; Klaus P. Stahl, Darmstadt; Volker Reiffenrath, Rossdorf; Ulrich Finkenzeller, Plankstadt; Ekkehard Bartmann, Erzhausen; Reinhard Hittich, Modautal, all of Germany; David Coates, Wimborne, Great Britain; Simon Greenfield; Graham Smith, both of Poole, Great Britain; Hans A. Kurmeier, Seeheim-Jugenheim; Dieter Dorsch, Darmstadt, both of Germany

[73] Assignee: Merck Patent Gesellschaft mit beschrankter Haftung, Darmstadt, Germany

[21] Appl. No.: 180,413

[22] Filed: Jan. 12, 1994

Related U.S. Application Data

[63] Continuation of Ser. No. 469,499, Mar. 21, 1990, abandoned.

[30] Foreign Application Priority Data

Jan. 27, 1989 [DE] Germany .................. 39 02 328.1
Jan. 27, 1989 [DE] Germany .................. 39 02 330.3
Apr. 25, 1989 [DE] Germany .................. 39 13 554.3

[51] Int. Cl.⁶ ..................... C09K 19/12; C09K 19/30
[52] U.S. Cl. ..................... 252/299.66; 252/299.63
[58] Field of Search ............. 252/299.63, 299.66

[56] References Cited

U.S. PATENT DOCUMENTS

| | | | |
|---|---|---|---|
| 4,659,502 | 4/1987 | Fearon et al. | 252/299.61 |
| 4,676,604 | 6/1987 | Petrzilka | 359/103 |
| 4,709,030 | 11/1987 | Petrzilka et al. | 544/242 |
| 4,846,998 | 7/1989 | Pohl et al. | 252/299.63 |
| 4,849,130 | 7/1989 | Dabrowski et al. | 252/299.61 |
| 4,871,469 | 10/1989 | Reiffenrath et al. | 252/299.61 |
| 4,911,863 | 3/1990 | Sage et al. | 252/299.65 |
| 4,970,022 | 11/1990 | Scheuble et al. | 252/299.61 |
| 5,120,467 | 6/1992 | Huynh-Ba et al. | 252/299.61 |
| 5,122,295 | 6/1992 | Weber et al. | 252/299.01 |
| 5,308,538 | 5/1994 | Weber et al. | 252/299.61 |
| 5,308,541 | 5/1994 | Hittich et al. | 252/299.63 |
| 5,308,542 | 5/1994 | Poetsch et al. | 252/299.63 |
| 5,318,721 | 6/1994 | Poetsch et al. | 252/299.63 |

FOREIGN PATENT DOCUMENTS 8706602 11/1987 WIPO .
8802357 4/1988 WIPO .

Primary Examiner—Gary Geist
Assistant Examiner—C. H. Kelly
Attorney, Agent, or Firm—Millen, White, Zelano & Branigan

[57] ABSTRACT

Biphenylylethanes of the formula I

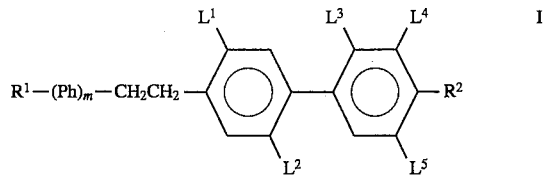

in which one of the radicals $R^1$ and $R^2$ is X and the other radical $R^1$ or $R^2$ is R—Y— where X is H, halogen, —$CF_3$, —$OCHF_2$, —$OCF_3$, —CN, —NCS or —$NO_2$, R is alkyl, fluoroalkyl, alkenyl or oxaalkyl and Y is O, S, —CO—O—, —O—CO—, —O—CO—O—, a single bond or—in the case where m=1—alternatively trans-1,4-cyclohexylene or

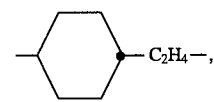

m is 1 or 2, Ph is in each case identical or different radicals selected from the group comprising 1,4-phenylene, 2-fluoro-1,4-phenylene, 3-fluoro-1,4-phenylene and 3,5-difluoro-1,4-phenylene, $L^3$ and $L^4$ are each H, or one of these radicals is alternatively F, $L^1$, $L^2$ and $L^5$ are each H or F, with the proviso that in the case where X=CN or $R^1$=—NCS, Y is trans-1,4-cyclohexylene or

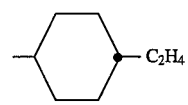

and/or m=2 and/or one of the radicals $L^1$, $L^2$ and $L^3$ is fluorine and/or Ph—CN is 2-fluoro-4-cyanophenyl or 3,5-difluoro-4-cyanophenyl, are suitable as components of liquid-crystalline phases.

31 Claims, No Drawings

BIPHENYLETHANES AND LIQUID-CRYSTALLINE PHASE

This application is a continuation, of application Ser. No. 07/469,499, filed Mar. 21, 1990 abandoned.

The invention relates to biphenylylethanes of the formula I

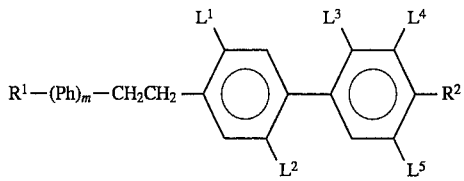

in which one of the radicals $R^1$ and $R^2$ is X and the other radical $R^1$ or $R^2$ is R—Y— where X is H, halogen, —$CF_3$, —$OCHF_2$, —$OCF_3$, —CN, —NCS or —$NO_2$, R is alkyl, fluoroalkyl, alkenyl or oxaalkyl and Y is O, S, —CO—O—, —O—CO—, —O—CO—O—, a single bond or—in the case where m=1—alternatively trans-1,4-cyclohexylene or

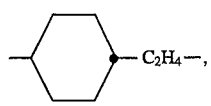

m is 1 or 2,

Ph is in each case identical or different radicals selected from the group comprising 1,4-phenylene, 2-fluoro-1,4-phenylene, 3-fluoro-1,4-phenylene and 3,5-difluoro-1,4-phenylene, $L^3$ and $L^4$ are each H, or one of these radicals is alternatively F, $L^1, L^2$ and $L^5$ are each H or F, with the proviso that in the case where X=CN or $R^1$=—NCS, Y is trans-1,4-cyclohexylene or

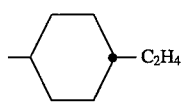

and/or m=2 and/or one of the radicals $L^1$, $L^2$ and $L^3$ is fluorine and/or Ph—CN is 2-fluoro-4-cyanophenyl or 3,5-difluoro-4-cyanophenyl.

The compounds of the formula I can be used as components of liquid-crystalline phases, in particular for displays based on the principle of the twisted cell, including highly twisted cells, the guest/host effect, the effect of deformation of aligned phases, or the effect of dynamic scattering.

Similar compounds are known, for example, from DOS 3,040,632 and 3,401,320. However, the compounds described therein are not biphenylylethanes, but instead cyclohexylphenylethanes.

Compounds of the formula

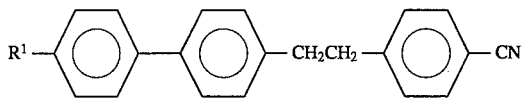

in which $R^1$ is n-alkyl or n-alkoxy are known from DOS 2,617,593. Compounds of the same formula in which $R^1$ is branched alkyl are known from DOS 2,736,772 as thermochromic materials and from JP 62/146,984 as materials for ferroelectric $S_c$ mixtures.

Compounds of the formula

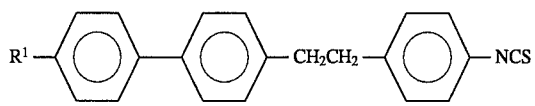

in which $R^1$ is n-pentoxy, 2-methylbutyl, n-butyl, n-pentyl, n-hexyl and n-heptyl are known from EP-OS 0,227,004.

The invention had the object of finding novel, stable liquid-crystalline or mesogenic compounds having high birefringence which are suitable as components of liquid-crystalline phases. This object has been achieved by the provision of the compounds of the formula I.

It has been found that the compounds of the formula I are preeminently suitable as components of liquid-crystalline phases. In particular, they can be used to prepare stable liquid-crystalline phases having relatively large optical anisotropy, positive dielectric anisotropy, low viscosity and high nematogeniety in combination with favourable low-temperature behaviour. The substances of formula I are particularly preferably suitable, for example, for use in mixtures for supertwist effects or for displays having an active matrix.

Surprisingly, it has been shown that the addition of compounds of the formula I gives liquid-crystalline phases which meet all the abovementioned criteria in an excellent manner.

In addition, the provision of the compounds of the formula I very generally considerably broadens the range of liquid-crystalline substances which are suitable, from various applicational points of view, for the preparation of nematic mixtures.

The compounds of the formula I have a broad field of application. Depending on the choice of substituents, these compounds can be used as base materials from which liquid-crystalline phases are predominantly composed; however, it is also possible to add compounds of the formula I to liquid-crystalline base materials from other classes of compounds, in order, for example, to optimize the dielectric and/or optical anisotropy of a dielectric of this type. The compounds of the formula I are furthermore suitable as intermediates for the preparation of other substances which can be used as components of liquid-crystalline phases.

In the pure state, the compounds of the formula I are colourless and form liquid-crystalline mesophases in a temperature range which is favourable for electro-optical use. They are very stable chemically, thermally and to light.

The invention thus relates to the compounds of the formula I and to the use of these compounds as components of liquid-crystalline phases. The invention furthermore relates to liquid-crystalline phases containing at least one compound of the formula I, and to liquid-crystal display elements which contain such phases.

Above and below, $R^1$, $R^2$, m, Y, Ph, $L^1$, $L^2$, $L^3$, $L^4$, $L^5$ and X have the meaning stated, unless expressly stated otherwise.

Particularly preferred biphenylethanes [sic] are those of the formula Ia,

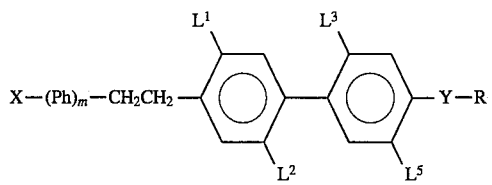

in which
R is alkyl, fluoroalkyl, alkenyl or oxaalkyl,
m is 1 or 2,
Y is O, S, CO—O, O—CO, O—CO—O, a single bond or—in the case where m=1—alternatively trans-1,4-cyclohexylene,
Ph is in each case identical or different radicals selected from the group comprising 1,4-phenylene, 2-fluoro-1,4-phenylene, 3-fluoro-1,4-phenylene and 3,5-difluoro-1,4-phenylene,
$L^1$, $L^2$,
$L^3$ and $L^5$ are each H or F,
X is F, Cl, —$CF_3$, —CN, —$OCF_3$, —$OCHF_2$, —NCS or —$NO_2$, with the proviso that
 a) in the case where X=—CN, Y is trans-1,4-cyclohexylene or m=2 and/or Ph—X is 2-fluoro-4-cyanophenyl, 3-fluoro-4-cyanophenyl or 3,5-difluoro-4-cyanophenyl and/or one or two of the radicals $L^1$, $L^2$, $L^3$ and $L^5$ is F, and
 b) in the case where X=NCS, Y=trans-1,4-cyclohexylene or m=2 and/or Ph—X is 2-fluoro-4-isothiocyanatophenyl, 3-fluoro-4-isothiocyanatophenyl or 3,5-difluoro-4-isothiocyanatophenyl and/or one or two of the radicals $L^1$, $L^2$, $L^3$ and $L^5$ is F and/or —Y—R is straight-chain alkyl having up to 3 C atoms,
and the biphenylylethanes of the formula Ib

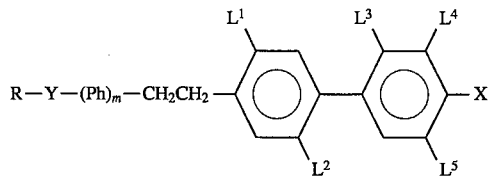

in which
R is alkyl, fluoroalkyl, alkenyl or oxaalkyl,
m is 1 or 2,
Y is O, S, CO—O, O—CO, O—CO—O, a single bond or— in the case where m=1—alternatively trans-1,4-cyclohexylene,
Ph is in each case identical or different radicals selected from the group comprising 1,4-phenylene, 2-fluoro-1,4-phenylene, 3-fluoro-1,4-phenylene and 3,5-difluoro-1,4-phenylene,
$L^1$, $L^3$,
and $L^4$ are each H, or one of these radicals is alternatively F,
$L^2$ and $L^5$ are each H or F, and
X is halogen, —$CF_3$, —CN, —$OCF_3$, —NCS or —$NO_2$, with the proviso that,
in the case where X=halogen, —CN or —$CF_3$, Y is trans-1,4-cyclohexylene or m=2 and/or $L^4$ and/or $L^5$ is fluorine (if X=halogen or —$CF_3$) or $L^4$ and $L^5$ or one of the radicals $L^1$, $L^2$ and $L^3$ (if X=CN) is fluorine.

Accordingly, the compounds of the formula Ia cover compounds of the preferred sub-formulae below:

in which X, Ph and R have the meaning indicated, and Y is O or a single bond.

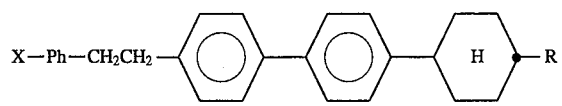

in which X, Ph and R have the meaning indicated.

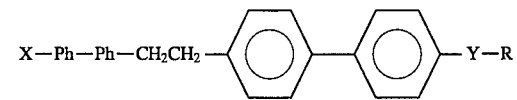

Accordingly, the compounds of the formula Ib cover compounds of the preferred sub-formulae below:

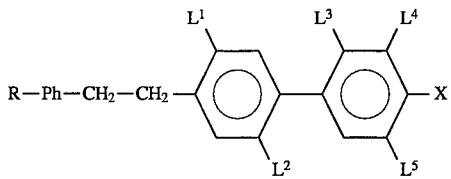

in which R, Ph, $L^1$, $L^2$, $L^3$, $L^4$, $L^5$ and X have the meaning indicated.

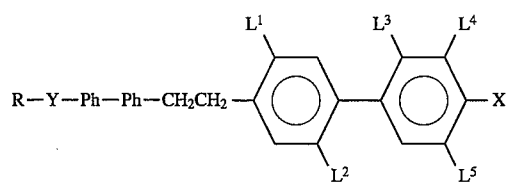

in which R, Ph, $L^1$, $L^2$, $L^3$, $L^4$, $L^5$ and X have the meaning indicated.

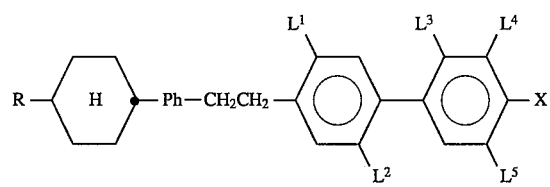

in which R, Ph, $L^1$, $L^2$, $L^3$, $L^4$, $L^5$ and X have the meaning indicated.

In the formula Ib1, X is preferably —$OCF_3$, —NCS or $NO_2$. Particularly preferred compounds are those of the formula Ib1 in which X is F, Cl or $CF_3$, and $L^4$ and/or $L^5$ is F.

Preferred compounds are also those of the formula Ib1 in which X is CN and $L^4$ and $L^5$ are fluorine or X is CN and one of the radicals $L^1$, $L^2$ and $L^3$ is fluorine.

In the formula [sic] Ib2 and Ib3, X is preferably —CN, F, Cl, —$CF_3$ or—$OCF_3$.

In the formula I and in the sub-formulae, X is preferably F, Cl, —$CF_3$, —$OCF_3$, $OCHF_2$, —NCS or —$NO_2$. Ph—X is preferably 3-fluoro-4-X-phenyl or 3,5-difluoro-4-X-phenyl. Particularly preferred meanings are 2-fluoro-4-cyanophenyl, 3-fluoro-4-cyanophenyl, 3,5-difluoro-4-cyanophenyl, 2-fluoro-4-isothiocyanatophenyl, 3-fluoro-4-isothiocyanatophenyl and 3,5-difluoro-4-isothiocyanatophenyl.

Particularly preferred compounds are furthermore those of the sub-formula Ia in which X is —CN or —NCS and one of the radicals $L^1$, $L^2$, $L^3$ and $L^5$ is F.

Likewise preferred biphenylethanes [sic] are those of the formula Ia2 in which X is —CN or —NCS, and biphenylethanes of the formula Ia3 in which X is —CN or —NCS.

Particularly preferred compounds are also those of the formula Ia4,

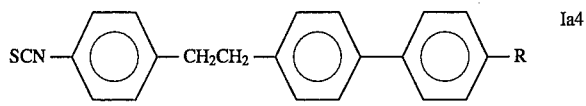

in which R is methyl, ethyl or n-propyl.

The radicals R preferably have up to 10 C atoms, in particular 2 to 7 C atoms.

If the groups R are alkyl radicals in which, in addition, one ("oxaalkyl") $CH_2$ group may be replaced by O atoms, they may be straight-chain or branched. They are preferably straight-chain, have 2, 3, 4, 5, 6 or 7 C atoms and accordingly are preferably ethyl, propyl, butyl, pentyl, hexyl, heptyl, ethoxy, propoxy, butoxy, pentoxy, hexoxy, heptoxy, 2-oxapropyl(=methoxymethyl), 2-(=ethoxymethyl) or 3-oxabutyl(=2-methoxyethyl), 2-, 3- or 4-oxapentyl, 2-, 3-, 4- or 5-oxahexyl, 2-, 3-, 4-, 5- or 6-oxaheptyl, furthermore methyl, octyl, nonyl, decyl, undecyl, dodecyl, tridecyl, tetradecyl, pentadecyl, methoxy, octoxy, nonoxy, decoxy, undecoxy, dodecoxy, tridecoxy, tetradecoxy, pentadecoxy, 2-, 3-, 4-, 5-, 6- or 7-oxaoctyl, 2-, 3-, 4-, 5-, 6-, 7- or 8-oxanonyl, 2-, 3-, 4-, 5-, 6-, 7-, 8- or 9-oxadecyl, 1,3-dioxabutyl(= methoxymethoxy), 1,3-, 1,4- or 2,4-dioxapentyl, 1,3-, 1,4-, 1,5-, 2,4-, 2,5- or 3,5-dioxahexyl, or 1,3-, 1,4-, 1,5-, 1,6-, 2,4-, 2,5-, 2,6-, 3,5-, 3,6- or 4,6-dioxaheptyl.

Particularly preferred alkyl radicals are also those in which one $CH_2$ group has been replaced by a —CH═CH group or by —CHF—.

m is preferably 1. X is preferably O, a single bond or trans-1,4-cyclohexylene; a single bond is particularly preferred. Y is preferably trans-1,4-cyclohexylene, —O— or a single bond.

Compounds of the formula I having branched wing groups R may occasionally be of importance due to better solubility in the customary liquid-crystalline base materials, but in particular as chiral dopes if they are optically active.

Branched groups of this type generally contain more than one chain branch. Preferred branched radical [sic] are isopropyl, 2-butyl(=1-methylpropyl), isobutyl(= 2-methylpropyl), 2-methylbutyl, isopentyl (=3-methylbutyl), 2-methylpentyl, 3-methylpentyl, 2-ethylhexyl, 2-propylpentyl, 2-octyl, isopropoxy, 2-methylpropoxy, 2-methylbutoxy, 3-methylbutoxy, 2-methylpentoxy, 3-methylpentoxy, 2-ethylhexoxy, 1-methylhexoxy, 1-methylheptoxy (=2-octyloxy), 2-oxa-3-methylbutyl, 3-oxa-4-methylpentyl, 4-methylhexyl, 2-nonyl, 2-decyl, 2-dodecyl, 6-methyloctoxy, 6-methyloctanoyloxy, 5-methylheptyloxycarbonyl, 2-methylbutyryloxy, 3-methylvaleryloxy, 4-methylhexanoyloxy, 2-methyl-3-oxapentyl or 2-methyl-3-oxahexyl.

In the case of compounds having branched wing groups, the formula I covers both the optical antipodes and the racemates, and mixtures thereof.

Of the compounds of the formula I and their subformulae, those are preferred in which at least one of the radicals present therein has one of the preferred meanings indicated.

Particularly preferred smaller groups of compounds according to the invention are those of the subformulae below:

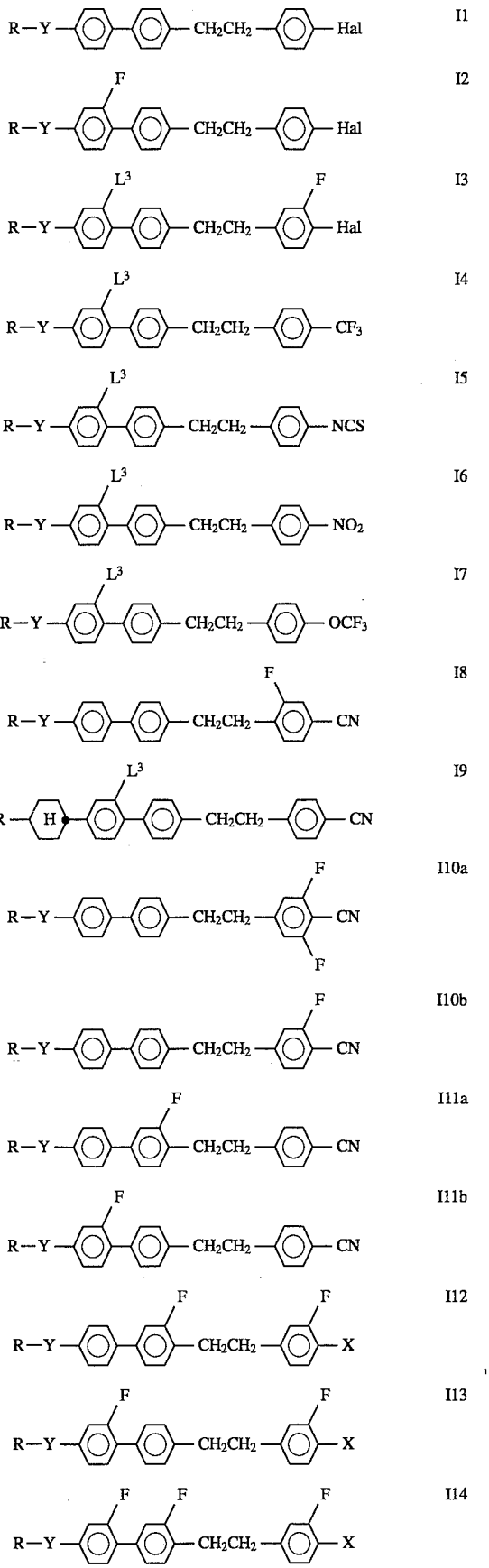

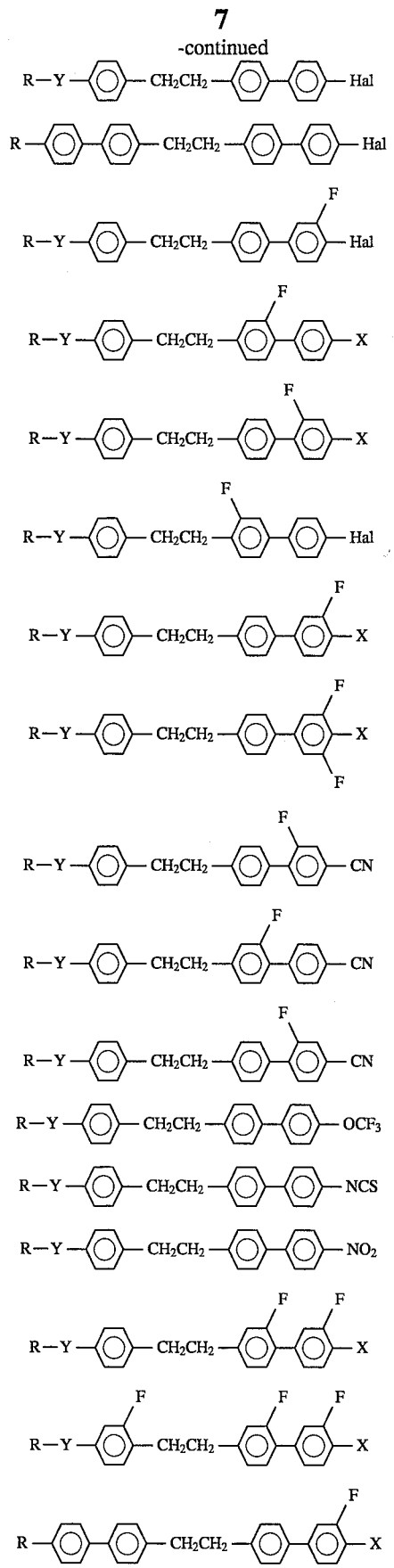
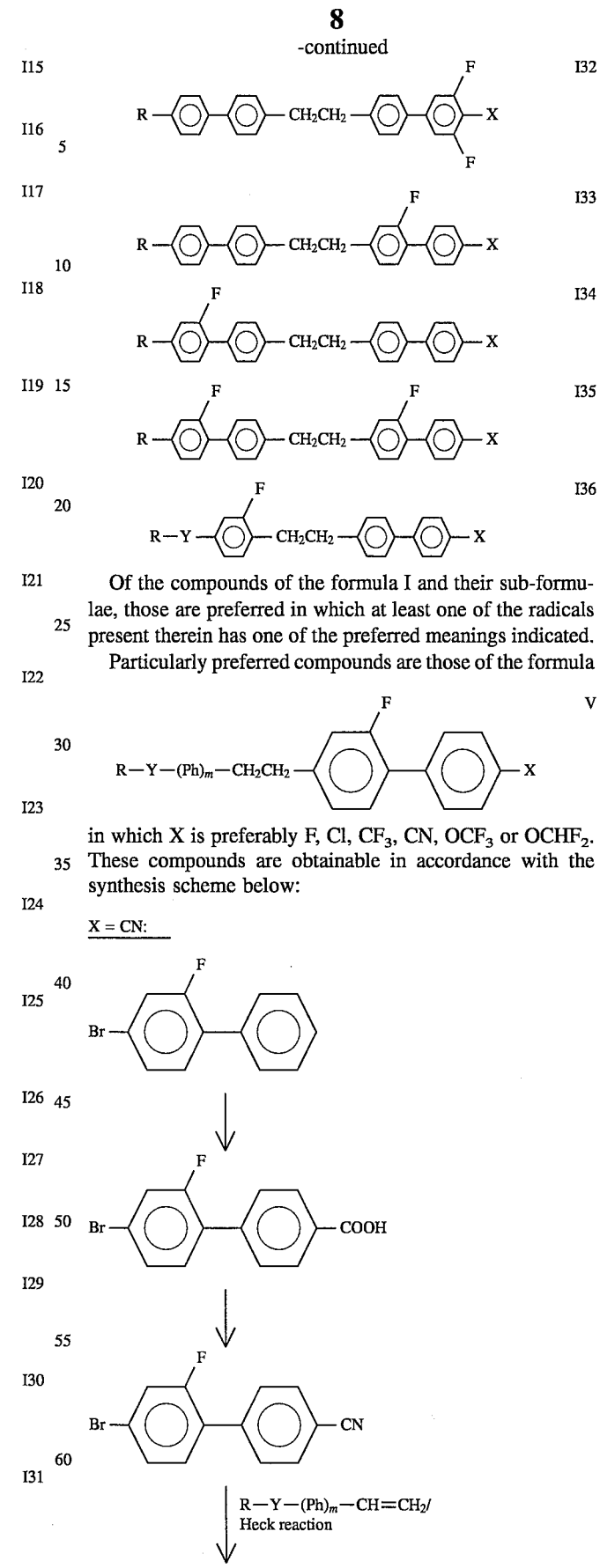

Of the compounds of the formula I and their sub-formulae, those are preferred in which at least one of the radicals present therein has one of the preferred meanings indicated.

Particularly preferred compounds are those of the formula V in which X is preferably F, Cl, $CF_3$, CN, $OCF_3$ or $OCHF_2$. These compounds are obtainable in accordance with the synthesis scheme below:

X = CN:

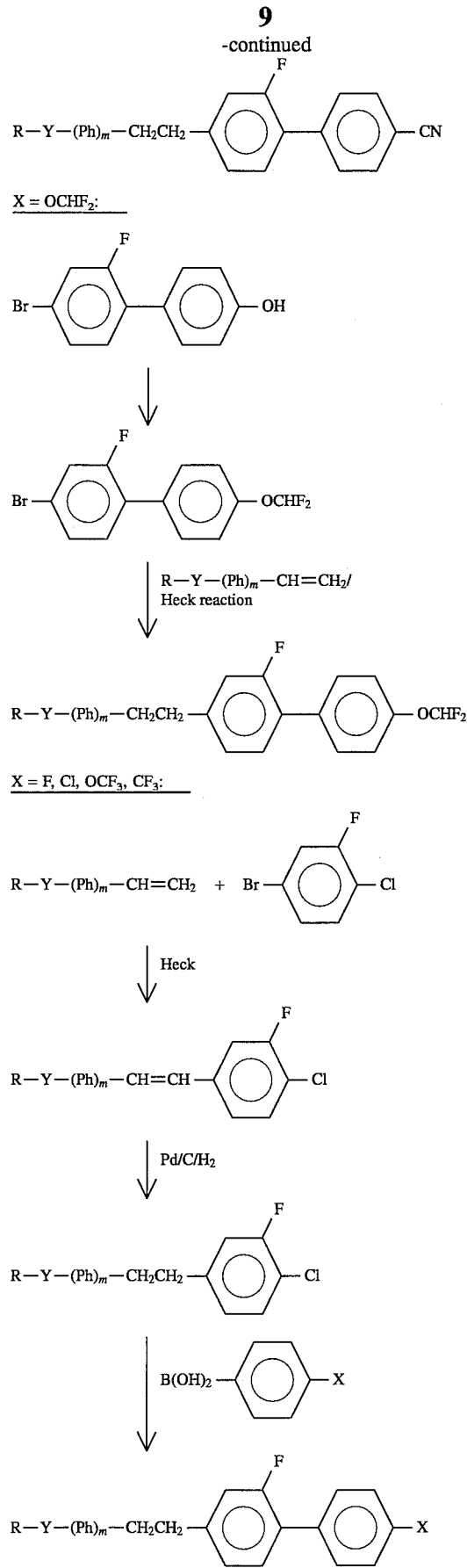

Regarding the lateral substitution by fluorine, the following substitution patterns are particularly preferred:

| $R^1$—(Ph)$_m$— | $L^1$ | $L^2$ | $L^3$ | $L^4$ | $L^5$ |
|---|---|---|---|---|---|
| R—Y—(Ph)$_m$— | H | F | H | H | H |
| R—Y—(Ph)$_m$— | H | H | H | F | H |
| R—Y—(Ph)$_m$— | H | H | H | F | F |
| R—Y—(Ph)$_m$— | H | F | H | F | H |
| R—Y—(Ph)$_m$— | H | F | H | F | F |
| R—Y—[3-F-phenylene]— | H | H | H | H | H |
| R—Y—[4-F-phenylene]— | H | F | H | H | H |
| X—(Ph)$_m$ | H | H | F | H | H |
| X—(Ph)$_m$ | F | H | H | H | H |
| X—(Ph)$_m$ | F | H | F | H | H |
| X—[3,4-diF-phenylene] | H | H | H | H | H |
| X—[3,4-diF-phenylene] | H | H | F | H | H |

Particularly preferred biphenylylethanes are those of the formula I

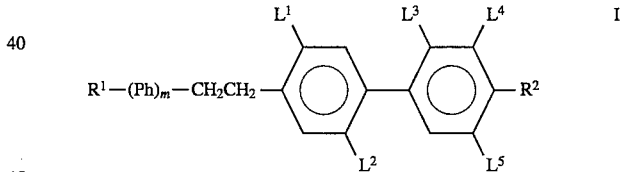

in which one of the radicals $R^1$ and $R^2$ is X and the other radical $R^1$ or $R^2$ is R—Y— where X is H, halogen, —CF$_3$, —OCHF$_2$, —OCF$_3$, —CN, —NCS or —NO$_2$, R is alkyl, fluoroalkyl, alkenyl or oxaalkyl and Y is O, S, —CO—O—, —O—CO—, —O—CO—O—, a single bond or—in the case where m=1—alternatively trans-1,4-cyclohexylene or

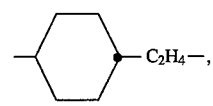

m is 1 or 2,

Ph is in each case identical or different radicals selected from the group comprising 1,4-phenylene, 2-fluoro-1,4-phenylene, 3-fluoro-1,4-phenylene and 3,5-difluoro-1,4-phenylene, $L^3$ and $L^4$ are each H, or one of these radicals is alternatively F, $L^1, L^2$
and $L^5$ are each H or F, with the proviso that
(1) where $R^2=X$ in the case where X=halogen, —CN or $CF_3$, Y is trans-1,4-cyclohexylene or

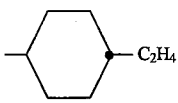

m=2 and/or $L^4$ and/or $L^5$ is fluorine (if X=halogen or —$CF_3$) or $L^4$ and $L^5$ or one of the radicals $L^1$, $L^2$ and $L^3$ (if X=CN) is fluorine, or (2) where $R^1=X$
 a) in the case where X=—CN, Y is trans-1,4-cyclohexylene or

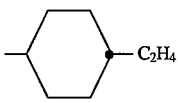

or m=2 and/or Ph-X is 2-fluoro-4-cyanophenyl, 3-fluoro-4-cyanophenyl or 3,5-difluoro-4-cyanophenyl and/or one or two of the radicals $L^1, L^2, L^3$ and $L^4$ is F, and b) in the case where X=NCS, Y=trans-1,4-cyclohexylene or is

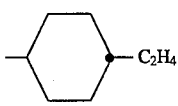

or m=2 and/or Ph-X is 2-fluoro-4-isothiocyanatophenyl, 3-fluoro-4-isothiocyanatophenyl or 3,5-difluoro-4-isothiocyanatophenyl and/or one or two of the radicals $L^1, L^2, L^3$ and $L^4$ is F and/or —Y—R is straight-chain alkyl having up to 3 C atoms.

Particularly preferred compounds are those of the sub-formula Ib in which Y is trans-1,4-cyclohexylene or

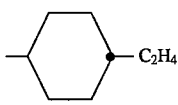

or m is 2.

Preferred compounds are those of the formula Ib in which $L^4$ and/or $L^5$ is fluorine or one of the radicals $L^1, L^2$ and $L^3$ is fluorine. In the former case ($L^4$ and/or $L^5$=F), X is preferably halogen or $CF_3$. In the latter case, X is preferably CN.

Preferred compounds of the sub-formula Ia are those in which Y is trans-1,4-cyclohexylene or

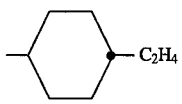

or m is 2. Ph—X is preferably 2-fluoro-4-cyanophenyl or 3,5-difluoro-4-cyanophenyl if X=CN. In the sub-formula Ia, one or two of the radicals $L^1, L^2, L^3$ and $L^4$ is preferably F.

The compounds of the formula I are prepared by methods known per se, as described in the literature (for example in the standard works such as Houben-Weyl, Methoden der Organischen Chemie [Methods of Organic Chemistry], Georg-Thieme-Verlag, Stuttgart), to be precise under reaction conditions which are known and suitable for the reactions mentioned. At the same time, use may also be made of variants which are known per se, but are not described here in greater detail.

If desired, the starting materials can also be formed in situ by not isolating them from the reaction mixture, but instead immediately reacting them further to form compounds of the formula I.

Thus, the compounds of the formula I can be prepared by catalyticallyhydrogenating a compound of the formula II

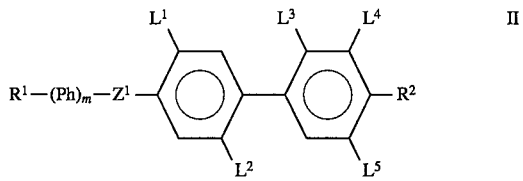

in which $Z^1$ is —CH=CH— or —C≡C—, under conditions which are known to those skilled in the art. In the formula II, $L^1, L^2, L^3, L^4, L^5$, m, $R^1$ and $R^2$ have the conditions [sic] indicated above. R is alkyl, fluoroalkyl or oxaalkyl.

The compounds of the formula II can be obtained in a manner known per se by the method of Wittig by reacting appropriate benzadehydes [sic] with appropriate phosphorus ylides or by Heck coupling from appropriate styrene compounds using haloaromatics (bromine or iodine), which are either known or can be prepared entirely analogously to known compounds.

Tolans of the formula II can also be prepared by coupling alkynyl zinc compounds with aryl halides analogously to the process described by A. O. King, E. Negishi, F. J. Villani and A. Silveira in J. Org. Chem. 43 (1978) 358.

Tolans of the formula II can also be prepared via the Fritsch-Buttenberg-Wiechell rearrangement (Ann. 279, 319, 327,332, 1984), in which the 1,1-diaryl-2-haloethylenes are rearranged in the presence of strong bases to form diarylacetylenes.

Tolans of the formula II can furthermore be prepared from 4-substituted phenyl- or cyclohexylacetylenes and aryl halides in the presence of a palladium catalyst, for example bis(triphenylphosphine)palladium(II) chloride, and copper(I) iodide (described in Synthesis (1980) 627 or Tetrahedron Letters 27 (1986) 1171).

The compounds used as starting materials, for example the materials of the formulae III and IV

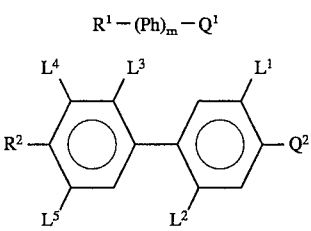

in which $Q^1$ and $Q^2$ are, for example, —$CH_2COCl$, —CH=$CH_2$, —CHO or —$CH_2Br$, are known or can be prepared entirely analogously to known compounds by standard methods.

Compounds according to the invention containing alkenyl groups can be prepared analogously to similar, known compounds by the Wittig reaction, the starting materials (conforming to the formula I, but one of the radicals $R^1$ and $R^2$ is —$(CH_2)_x$—CHO or, for example, —$(CH_2)_x$—Br, X=0 to 5) being accessible analogously to the methods described above.

The compounds of the formula I can furthermore be prepared by cross-coupling in accordance with DOS 3,608,502, DOS 3,632,410 or DOS 3,736,489 or by Wolff-Kishner reduction of appropriate methylene ketones, which are themselves readily accessible by Friedel-Crafts acylations from the corresponding arylacetyl chlorides and corresponding benzene or biphenyl precursors.

Particularly preferred synthesis variants of the preferred compounds of the sub-formula Ia in which m=1 and $L^1=L^2=H$ are indicated in the scheme below:

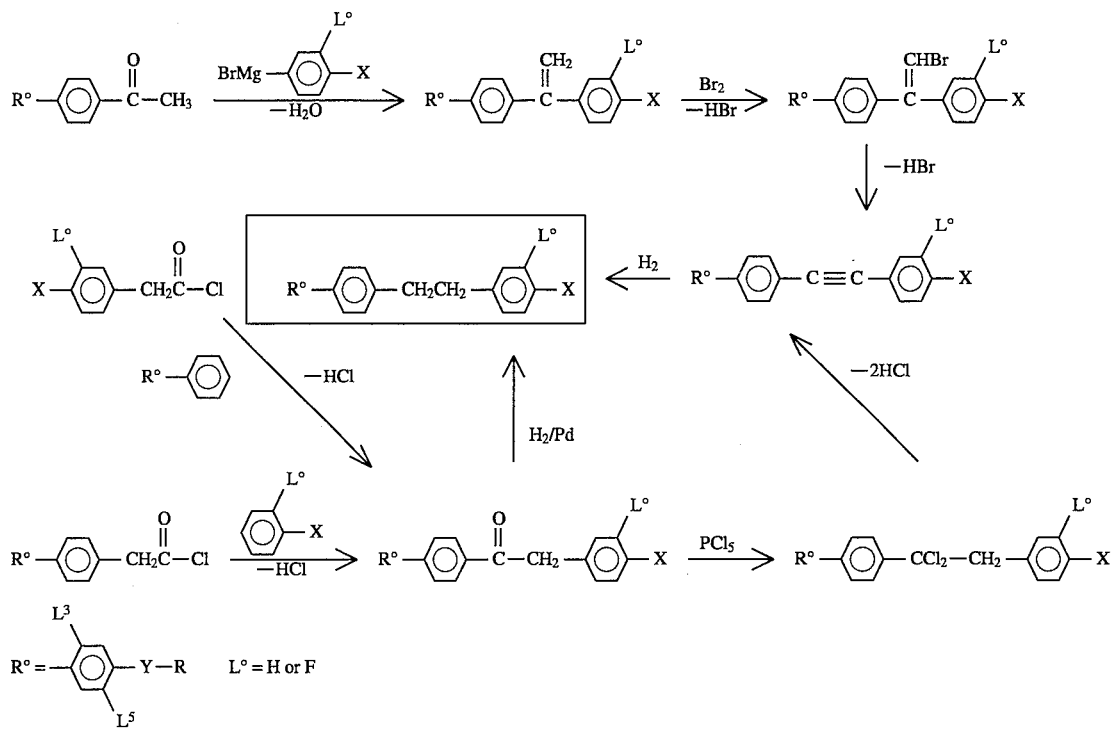

Preferably, $L^3=F$, $L^5=H$,

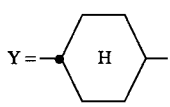

or a single bond, R=n-alkyl, X=F, Cl, $CF_3$ or $OCF_3$. $L^o$ is preferably H.

Particularly preferred compounds are those of the formulae I31 to 36, I18, I19, I21 and I22. X here is preferably CN, F, Cl, $CF_3$, $OCF_3$ or $OCHF_2$, in particular preferably CN, F or Cl. Y is preferably trans-1,4-cyclohexylene (in particular in I22) or a single bond.

Further particularly preferred compounds according to the invention are listed in the two tables below. Cy=trans-1,4-cyclohexylene, Ph=1,4-phenylene,

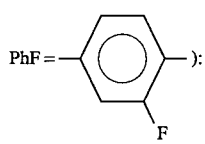

| n | Y  | $L^3$ | $L^A$ | $L^B$ | X  |
|---|----|-------|-------|-------|-----|
| 3 | —  | F | H | H | CN |
| 5 | —  | F | H | H | CN |
| 3 | —  | F | F | H | CN |
| 2 | —  | F | H | H | Cl |
| 3 | —  | F | H | H | Cl |
| 3 | —  | F | H | H | CN |
| 3 | Cy | H | F | H | CN |
| 5 | Cy | H | F | H | CN |
| 3 | Cy | H | F | F | CN |
| 5 | Cy | H | F | F | CN |
| 3 | —  | H | H | H | Cl |
| 5 | —  | H | H | H | Cl |
| 3 | —  | H | F | H | Cl |
| 5 | —  | H | F | H | Cl |
| 3 | Cy | F | H | H | CN |
| 5 | Cy | F | H | H | CN |

| n | Y | $L^3$ | $L^A$ | $L^B$ | X |
|---|---|---|---|---|---|
| 3 | Cy | F | F | H | CN |
| 5 | Cy | F | F | H | CN |
| 3 | Cy | F | F | H | F |

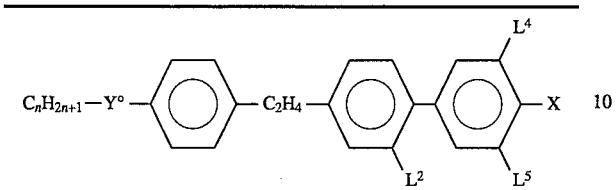

| n | $Y^o$ | $L^2$ | $L^4$ | $L^5$ | X |
|---|---|---|---|---|---|
| 3 | Cy | H | F | H | CN |
| 5 | Cy | H | F | H | CN |
| 3 | Cy | H | F | F | CN |
| 5 | Cy | H | F | F | CN |
| 3 | Ph | H | F | H | CN |
| 5 | Ph | H | F | H | CN |
| 3 | Ph | H | F | F | CN |
| 5 | Ph | H | F | F | CN |
| 3 | Ph | F | H | H | CN |
| 5 | Ph | F | H | H | CN |
| 3 | PhF | H | H | H | CN |
| 3 | Ph | F | H | H | CN |
| 3 | — | F | H | H | CN |
| 3 | — | F | H | H | Cl |
| 3 | — | F | H | H | F |
| 3 | — | F | H | H | $CF_3$ |
| 3 | — | F | H | H | $OCF_3$ |
| 3 | — | F | H | H | $OCHF_2$ |
| 5 | — | F | H | H | CN |
| 5 | — | F | H | H | Cl |
| 5 | — | F | H | H | F |

| n | $Y^o$ | $L^2$ | $L^4$ | $L^5$ | X |
|---|---|---|---|---|---|
| 5 | — | F | H | H | $CF_3$ |
| 5 | — | F | H | H | $OCF_3$ |
| 5 | — | F | H | H | $OCHF_2$ |
| 2 | — | F | H | H | CN |
| 2 | — | F | H | H | Cl |
| 2 | — | F | H | H | F |
| 2 | — | F | H | H | $CF_3$ |
| 2 | — | F | H | H | $OCF_3$ |
| 2 | — | F | H | H | $OCHF_2$ |
| 4 | — | F | H | H | CN |
| 4 | — | F | H | H | Cl |
| 4 | — | F | H | H | F |
| 4 | — | F | H | H | $CF_3$ |
| 4 | — | F | H | H | $OCF_3$ |
| 4 | — | F | H | H | $OCHF_2$ |
| 3 | — | H | F | H | Cl |
| 5 | — | H | F | H | Cl |
| 3 | — | H | F | H | F |
| 5 | — | H | F | H | F |
| 2 | — | H | H | H | F |
| 3 | — | H | H | H | F |
| 4 | — | H | H | H | F |
| 5 | — | H | H | H | F |
| 2 | — | H | H | H | Cl |
| 3 | — | H | H | H | Cl |
| 4 | — | H | H | H | Cl |
| 5 | — | H | H | H | Cl |
| 2 | — | H | F | H | F |
| 4 | — | H | F | H | F |

Further possible synthesis of particularly preferred compounds are indicated in schemes A to D below (Y is preferably other than a single bond if the molecule contains a 3-fluoro-4-cynophenyl group):

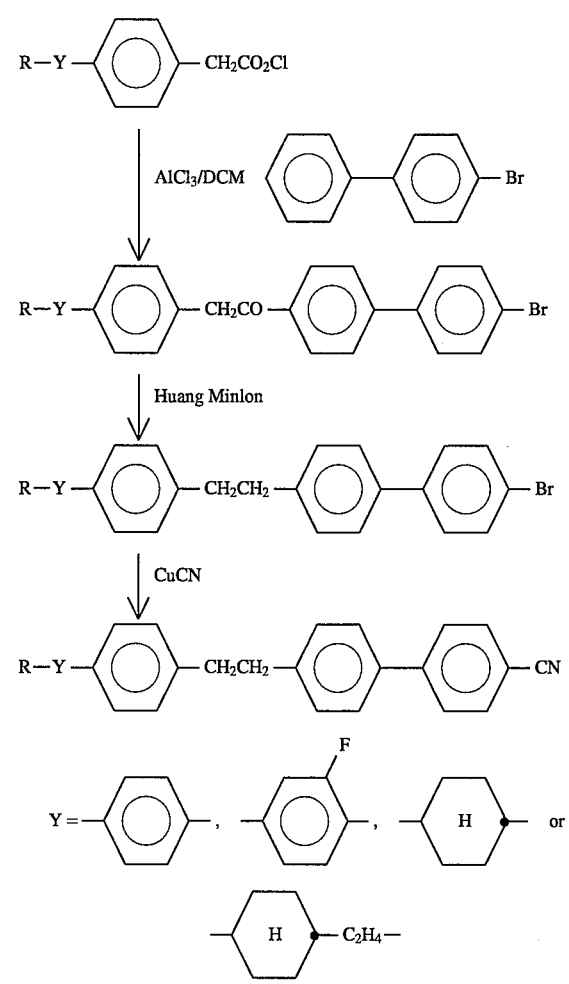

R=n-alkyl having up to 10 C atoms

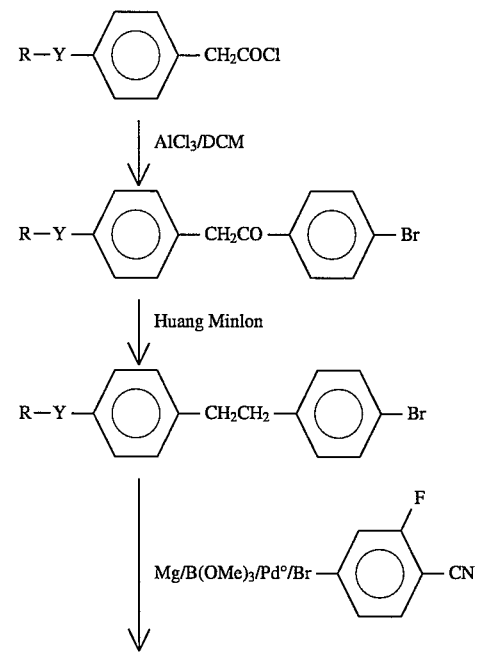

Scheme B

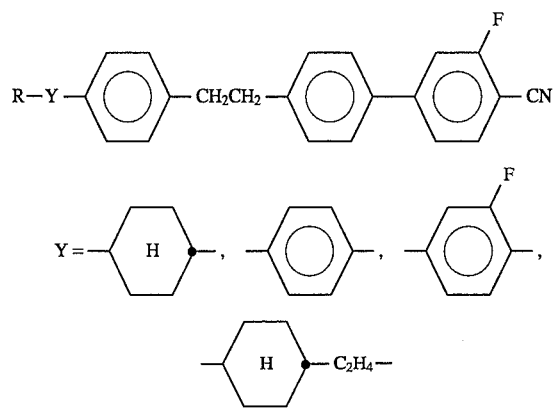

or a single bond R=n-alkyl having up to 10 C atoms

Scheme C:

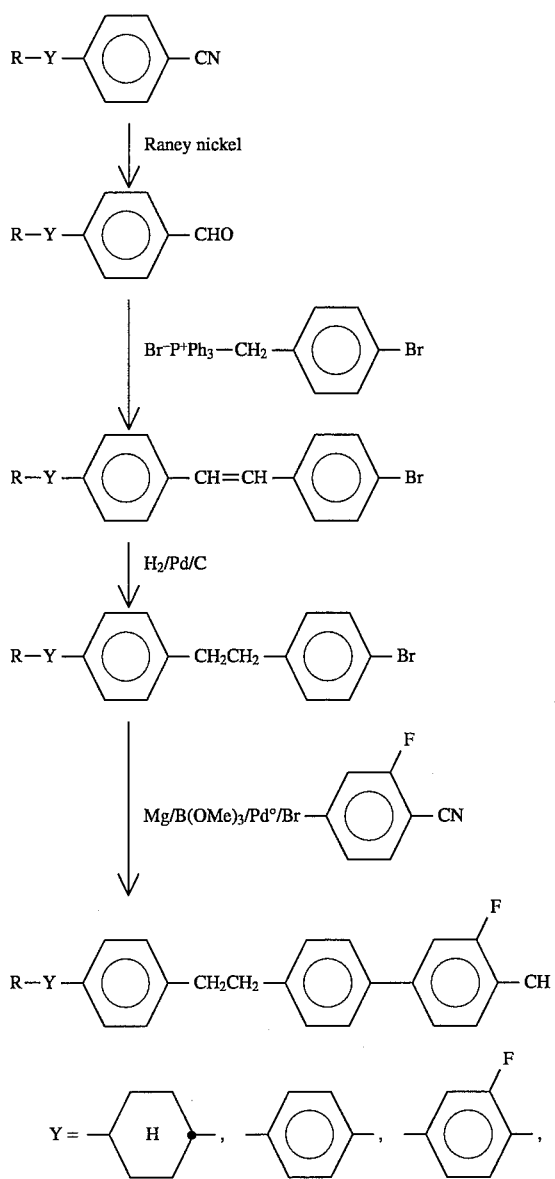

Scheme C:

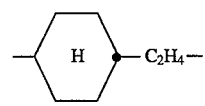

or a single bond R=n-alkyl having up to 10 C atoms

Scheme D:

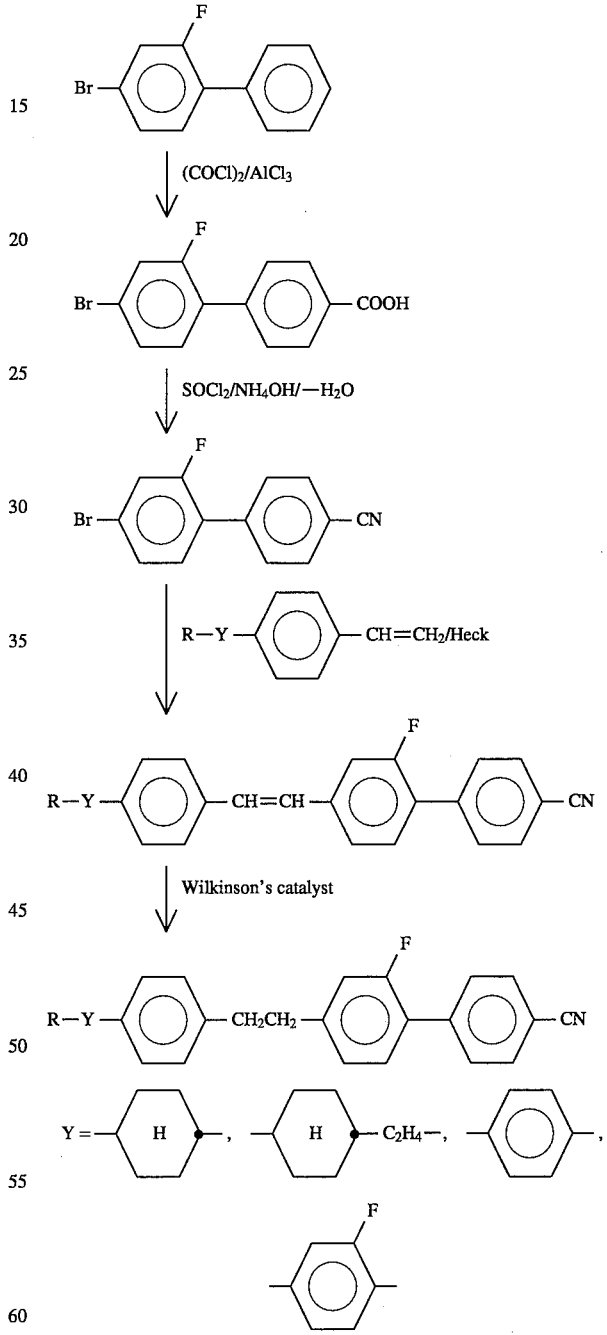

or a single bond R=n-alkyl having up to 10 C atoms

The compounds according to the invention where X=CN are particularly suitable as components of LC mixtures for PDLCs (polymer dispersed liquid crystals) or PNs (polymer network). In the trinuclear compounds of this type, $R^2$ is preferably CN and $L^2$ is preferably F. Tetranuclear CN compounds (m=2 or Y=trans-1,4-cyclohexylene or

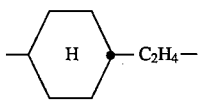

are particularly preferred.

The liquid-crystalline media according to the invention preferably contain 2 to 40, in particular 4 to 30, components as further components besides one or more compounds according to the invention. These media very particularly preferably contain 3 to 20 components besides one or more compounds according to the invention. The other components are preferably selected from nematic or nematogenic (monotropic or isotropic) substances, in particular substances from the classes of the azoxybenzenes, benzylideneanilines, biphenyls, terphenyls, phenyl or cyclohexyl benzoates, phenyl or cyclohexyl esters of cyclohexanecarboxylic acid, phenyl or cyclohexyl esters of cyclohexylbenzoic acid, phenyl or cyclohexyl esters of cyclohexylcyclohexanecarboxylic acid, cyclohexylphenyl esters of benzoic acid, of cyclohexanecarboxylic acid and of cyclohexylcyclohexanecarboxylic acid, phenylcyclohexanes, cyclohexylbiphenyls, phenylcyclohexylcyclohexanes, cyclohexylcyclohexanes, cyclohexylcyclohexenes, cyclohexylcyclohexylcyclohexenes, 1,4-bis-cyclohexylbenzenes, 4,4'-bis-cyclohexylbiphenyls, phenyl- or cyclohexylpyrimidines, phenyl- or cyclohexylpyridines, phenyl- or cyclohexyldioxanes, phenyl- or cyclohexyl-1,3-dithianes, 1,2-diphenylethanes, 1,2-dicyclohexylethanes, 1-phenyl-2-cyclohexylethanes, 1-cyclohexyl-2-(4-phenylcyclohexyl)ethanes, 1-cyclohexyl-2-biphenylylethanes, 1-phenyl-2-cyclohexylphenylethanes, optionally halogenated stilbenes, benzyl phenyl ethers, tolans and substituted cinnamic acids. The 1,4-phenylene groups in these compounds may also be fluorinated.

The most important compounds suitable as further components of media according to the invention can be characterized by the formulae 1, 2, 3, 4 and 5:

| | |
|---|---|
| R'—L—E—R" | 1 |
| R'—L—COO—E—R" | 2 |
| R'—L—OOC—E—R" | 3 |
| R'—L—CH$_2$CH$_2$—E—R" | 4 |
| R'—L—C≡C—E—R" | 5 |

In the formulae 1, 2, 3, 4 and 5, L and E, which may be identical or different, are in each case, independently of one another, a bivalent radical from the group formed —Phe—, —Cyc—, —Phe—Phe, —Phe—Cyc—, —Cyc—Cyc—, Pyr, —Dio—, —G—Phe— and —G—Cyc— and their mirror images, where Phe is unsubstituted or fluorine-substituted 1,4-phenylene, Cyc is trans-1,4-cyclohexylene or 1,4-cyclohexenylene, Pyr is pyrimidine-2,5-diyl or pyridine-2,5-diyl, Dio is 1,3-dioxane-2,5-diyl and G is 2-(transl, 4-cyclohexyl)ethyl, pyrimidine-2,5-diyl, pyridine-2,5-diyl or 1,3-dioxane-2,5-diyl.

One of the radicals L and E is preferably Cyc, Phe or Pyr. E is preferably Cyc, Phe or Phe—Cyc. The media according to the invention preferably contain one or more components selected from the compounds of the formulae 1, 2, 3, 4 and 5 in which L and E are selected from the group comprising Cyc, Phe and Pyr and simultaneously one or more components selected from the compounds of the formulae 1, 2, 3, 4 and 5 in which one of the radicals L and E is selected from the group comprising Cyc, Phe and Pyr and the other radical is selected from the group comprising —Phe—Phe—, —Phe—Cyc—, —Cyc—Cyc—, —G—Phe— and —G—Cyc—, and optionally one or more components selected from the compounds of the formulae 1, 2, 3, 4 and 5 in which the radicals L and E are selected from the group comprising —Phe—Cyc—, —Cyc—Cyc—, G—Phe— and —G—Cyc—.

In the compounds of the sub-formulae 1a, 2a, 3a, 4a and 5a, R' and R" are in each case, independently of one another, alkyl, alkenyl, alkoxy, alkenyloxy or alkanoyloxy having up to 8 carbon atoms. In most of these compounds, R' and R" are different from one another, one of these radicals usually being alkyl or alkenyl. In the compounds of the sub-formulae 1b, 2b, 3b, 4b and 5b, R" is —CN, —CF$_3$, F, Cl or —NCS; in this case, R has the meaning given for the compounds of the sub-formulae 1a to 5a and is preferably alkyl or alkenyl. However, other variants of the proposed substituents in the compounds of the formulae 1, 2, 3, 4 and 5 are common. Many such substances or alternatively mixtures thereof are commercially available. All these substances can be obtained by methods which are known from the literature or analogously thereto.

Besides components from the group comprising the compounds 1a, 2a, 3a, 4a and 5a (Group 1), the media according to the invention preferably also contain components from the group comprising the compounds 1b, 2b, 3b, 4b and 5b (Group 2), whose proportions are preferably as follows:

Group 1:20 to 90%, in particular 30 to 90%,

Group 2:10 to 80%, in particular 10 to 50%, the sum of the proportions of the compounds according to the invention and of the compounds from Groups 1 and 2 adding up to 100%.

The media according to the invention preferably contain 1 to 40%, in particular preferably 5 to 30%, of compounds according to the invention. Further preferred media are those which contain more than 40%, in particular 45 to 90%, of compounds according to the invention. The media preferably contain three, four or five compounds according to the invention.

The phases according to the invention are prepared in a manner which is customary per se. In general, the components are dissolved in one another, expediently at elevated temperature.

By means of suitable additives, the liquid-crystalline phases can be modified in accordance with the invention in a manner such that they can be used in all types of liquid-crystal display elements which have hitherto been disclosed.

Additives of this type are known to those skilled in the art and are described in detail in the literature. For example, conductive salts, preferably ethyldimethyldodecylammonium 4-hexyloxybenzate, tetrabutylammonium tetraphenylborate, or complex salts of crown ethers (cf,for example I Haller Cryst. et al., Mol. Cryst.Liq.1 Vol. 24, pages 249–258 (1973), can be added to improve the conductivity, dichroic dyes can be added for the production of coloured guest-host systems, or substances can be added to modify the dielectric anisotropy, the viscosity and/or the orientation of the nematic phases. Substances of this type are described for example, in DE-OS 2,209,127, 2,240,864, 2,321,632, 2,338,281, 2,450,088, 2,637,430, 2,853,728 and 2,902,177.

The examples below are intended to illustrate the invention without representing a limitation. mp.=melting point, cp.=clear point. Above and below, percentages are per cent by weight; all temperatures are indicated in degrees Celsius. "Customary work-up" means that water is added, the mixture is extracted with methylene chloride, the organic phase is separated off, dried and evaporated, and the product is purified by crystallization and/or chromatography.

EXAMPLE 1

A solution of 9.5 g of 1-(p-fluorophenyl)-2-(4'-n-pentylbiphenyl-4-yl)ethene [obtained by Heck coupling of 4-fluorostyrene with 4-bromo-4'-n-pentylbiphenyl] in 100 ml of tetrahydrofuran is hydrogenated in the presence of Pd/C until the take-up of H is complete. Customary work-up gives 1-(p-fluorophenyl)-2-(4'-n-pentylbiphenyl-4-yl)ethane, mp. 60°, cp. 109°.

The following are prepared analogously:

1-(p-fluorophenyl)-2-(4'-n-propylbiphenyl-4-yl)ethane, mp. 104°
1-(p-chlorophenyl)-2-(4'-n-propylbiphenyl-4-yl)ethane
1-(3-fluoro-4-chlorophenyl)-2-(4'-n-propylbiphenyl-4-yl)ethane
1-(p-chlorophenyl)-2-(4'-n-propyl-2'-fluorobiphenyl-4-yl)ethane, mp. 63.6°
1-(p-trifluoromethylphenyl)-2-(4'-ethylbiphenyl-4-yl)ethane
1-(p-trifluoromethylphenyl)-2-(4'-n-propylbiphenyl-4-yl)ethane, mp. 128°
1-(p-trifluoromethylphenyl)-2-(4'-n-butylbiphenyl-4-yl)ethane
1-(p-trifluoromethylphenyl)-2-(4'-n-pentylbiphenyl-4-yl)ethane, mp. 85°, cp. 126°
1-(p-trifluoromethylphenyl)-2-(4'-n-propyl-2'-fluorobiphenyl-4-yl)ethane
1-(p-trifluoromethylphenyl)-2-(4'-n-pentyl-2'-fluorobiphenyl-4-yl)ethane
1-(p-trifluoromethoxyphenyl)-2-(4'-ethylbiphenyl-4-yl)ethane
1-(p-trifluoromethoxyphenyl)-2-(4'-n-propylbiphenyl-4-yl)ethane, mp. 76°, cp. 141°
1-(p-trifluoromethoxyphenyl)-2-(4'-n-butylbiphenyl-4-yl)ethane,
1-(p-trifluoromethoxyphenyl)-2-(4'-n-pentylbiphenyl-4-yl)ethane, mp. 62°, cp. 136°
1-(p-trifluoromethoxyphenyl)-2-(4'-n-propyl-2'-fluorobiphenyl-4-yl)ethane
1-(p-trifluoromethoxyphenyl)-2-(4'-n-pentyl-2'-fluorobiphenyl-4-yl)ethane
1-(p-difluoromethoxyphenyl)-2-(4'-ethylbiphenyl-4-yl)ethane
1-(p-difluoromethoxyphenyl)-2-(4'-n-propylbiphenyl-4-yl)ethane
1-(p-difluoromethoxyphenyl)-2-(4'-n-butylbiphenyl-4-yl)ethane
1-(p-difluoromethoxyphenyl)-2-(4'-n-propyl-2'-fluorobiphenyl-4-yl)ethane
1-(p-difluoromethoxyphenyl)-2-(4'-n-pentyl-2'-fluorobiphenyl-4-yl)ethane
1-(p-chlorophenyl)-2-(4'-n-butyl-2'-fluorobiphenyl-4-yl)ethane
1-(p-chlorophenyl)-2-(4'-n-pentyl-2'-fluorobiphenyl-4-yl)ethane, mp. 49°, cp. 82°
1-(p-chlorophenyl)-2-(4'-n-heptyl-2'-fluorobiphenyl-4-yl)ethane
1-(p-chlorophenyl)-2-(4'-n-ethyl-2'-fluorobiphenyl-4-yl)ethane, mp. 62.4°
1-(p-fluorophenyl)-2-(4'-ethyl-2'-fluorobiphenyl-4-yl)ethane
1-(p-fluorophenyl)-2-(4'-n-propyl-2'-fluorobiphenyl-4-yl)ethane
1-(p-fluorophenyl)-2-(4'-n-butyl-2'-fluorobiphenyl-4-yl)ethane
1-(p-fluorophenyl)-2-(4'-n-pentyl-2'-fluorobiphenyl-4-yl)ethane, mp. 35°, cp. 54°
1-(p-fluorophenyl)-2-(4'-n-heptyl-2'-fluorobiphenyl-4-yl)ethane
1-(p-fluorophenyl)-2-[4'-(trans-4-ethylcyclohexyl)-2'-fluorobiphenyl-4-yl)ethane
1-(p-fluorophenyl)-2-[4'-(trans-4-n-propylcyclohexyl)-2'-fluorobiphenyl-4-yl)ethane
1-(p-fluorophenyl)-2-[4'-(trans-4-n-butylcyclohexyl)-2'-fluorobiphenyl-4-yl)ethane
1-(p-fluorophenyl)-2-[4'-(trans-4-n-pentylcyclohexyl)-2'-fluorobiphenyl-4-yl)ethane, mp. 68°, cp. 206°
1-(p-fluorophenyl)-2-[4'-(trans-4-n-heptylcyclohexyl)-2'-fluorobiphenyl-4-yl)ethane
1-(p-chlorophenyl-2-[4'-(trans-4-ethylcyclohexyl)-2'-fluorobiphenyl-4-yl)ethane
1-(p-chlorophenyl-2-[4'-(trans-4-n-propylcyclohexyl)-2'-fluorobiphenyl-4-yl)ethane
1-(p-chlorophenyl-2-[4'-(trans-4-n-butylcyclohexyl)-2'-fluorobiphenyl-4-yl)ethane
1-(p-chlorophenyl-2-[4'-(trans-4-n-pentylcyclohexyl)-2'-fluorobiphenyl-4-yl)ethane
1-(p-chlorophenyl-2-[4'-(trans-4-n-heptylcyclohexyl)-2'-fluorobiphenyl-4-yl)ethane
1-(p-fluorophenyl)-2-(4'-n-butoxybiphenyl-4-yl)ethane, mp. 102°, cp. 145°
1-(p-fluorophenyl)-2-(4'-n-propoxybiphenyl-4-yl)ethane
1-(p-fluorophenyl)-2-(4'-n-ethoxybiphenyl-4-yl)ethane
1-(3,5-difluorophenyl)-2-(4'-ethylbiphenyl-4-yl)ethane
1-(3,5-difluorophenyl)-2-(4'-n-propylbiphenyl-4-yl)ethane
1-(3,5-difluorophenyl)-2-(4'-n-butylbiphenyl-4-yl)ethane
1-(3,5-difluorophenyl)-2-(4'-n-pentylbiphenyl-4-yl)ethane, mp. 59°
1-(p-chlorophenyl)-2-(4'-ethylbiphenyl-4-yl)ethane
1-(p-chlorophenyl)-2-(4'-n-propylbiphenyl-4-yl)ethane
1-(p-chlorophenyl)-2-(4'-n-butylbiphenyl-4-yl)ethane
1-(p-chlorophenyl)-2-(4'-n-pentylbiphenyl-4-yl)ethane, mp. 129°

EXAMPLE 2

A solution of 10.6 g of 1-(p-n-propylphenyl)-2-(4'-fluorobiphenyl-4-yl)ethene [obtained by Heck coupling of 4-propylstyrene with 4-bromo-4'-n-fluorobiphenyl] in 200 ml of tetrahydrofuran is hydrogenated in the presence of Pd/C until the take-up H of is complete. Customary work-up gives 1-(p-propylphenyl)-2-(4'-fluorobiphenyl-4-yl)ethane, mp. 97°.

1-(p-ethoxyphenyl)-2-(4'-trifluoromethoxybiphenyl-4-yl)ethane, mp. 165°
1-(p-ethylphenyl)-2-(4'-trifluoromethoxybiphenyl-4-yl)ethane
1-(p-n-propylphenyl)-2-(4'-trifluoromethoxybiphenyl-4-yl)ethane, mp. 97°, cp. 137°
1-(p-butylphenyl)-2-(4'-trifluoromethoxybiphenyl-4-yl)ethane
1-(p-pentylphenyl)-2-(4'-trifluoromethoxybiphenyl-4-yl)ethane
1-(p-n-propylphenyl)-2-(4'-chloro-3'-fluorobiphenyl-4-yl)ethane, mp. 60°, cp. 65°
1-(p-n-butylphenyl)-2-(4'-chloro-3'-fluorobiphenyl-4-yl)ethane
1-(p-n-pentylphenyl)-2-(4'-chloro-3'-fluorobiphenyl-4-yl)ethane
1-(p-ethoxyphenyl)-2-(4'-difluoromethoxybiphenyl-4-yl)ethane, mp. 153°
1-(p-ethylphenyl)-2-(4'-difluoromethoxybiphenyl-4-yl)ethane
1-(p-n-propylphenyl)-2-(4'-difluoromethoxybiphenyl-4-yl)ethane, mp. 131°
1-(p-n-butylphenyl)-2-(4'-difluoromethoxybiphenyl-4-yl)ethane 1-(p-n-pentylphenyl)-2-(4'-difluoromethoxybiphenyl-4-yl)ethane
1-(p-ethoxyphenyl)-2-(4'-fluorobiphenyl-4-yl)ethane, mp. 121°, cp. 130°
1-(p-ethylphenyl)-2-(4'-fluorobiphenyl-4-yl)ethane
1-(p-n-propylphenyl)-2-(4'-fluorobiphenyl-4-yl)ethane
1-(p-n-butylphenyl)-2-(4'-fluorobiphenyl-4-yl)ethane
1-(p-n-pentylphenyl)-2-(4'-fluorobiphenyl-4-yl)ethane
1-(p-ethylphenyl)-2-(2',4'-difluorobiphenyl-4-yl)ethane
1-(p-n-propylphenyl)-2-(2',4'-difluorobiphenyl-4-yl)ethane
1-(p-n-butylphenyl)-2-(2',4'-difluorobiphenyl-4-yl)ethane
1-(p-n-pentylphenyl)-2-(2',4'-difluorobiphenyl-4-yl)ethane, mp. 40°, cp. 50°
1-(p-ethylphenyl)-2-(3',4'-difluorobiphenyl-4-yl)ethane
1-(p-n-propylphenyl)-2-(3',440 ,-difluorobiphenyl-4-yl)ethane 1-(p-n-butylphenyl)-2-(3',4'-difluorobiphenyl-4-yl)ethane
1-(p-n-pentylphenyl)-2-(3',4'-difluorobiphenyl-4-yl)ethane, mp. 46°
1-(p-ethylphenyl)-2-(3'-fluoro-4'-chlorobiphenyl-4-yl)ethane
1-(p-n-propylphenyl)-2-(3'-fluoro-4'-chlorobiphenyl-4-yl)ethane
1-(p-n-butylphenyl)-2-(3'-fluoro-4'-chlorobiphenyl-4-yl)ethane
1-(p-n-pentylphenyl)-2-(3'-fluoro-4'-chlorobiphenyl-4-yl)ethane
1-(2-fluoro-4-n-propylphenyl)-2-(4'-fluorobiphenyl-4-yl)ethane
1-(2-fluoro-4-n-pentylphenyl)-2-(4'-fluorobiphenyl-4-yl)ethane
1-(2-fluoro-4-n-propylphenyl)-2-(4'-chlorobiphenyl-4-yl)ethane
1-(2-fluoro-4-n-pentylphenyl)-2-(4'-chlorobiphenyl-4-yl)ethane
1-(2-fluoro-4-n-propylphenyl)-2-(4'-cyanobiphenyl-4-yl)ethane
1-(2-fluoro-4-n-pentylphenyl)-2-(4'-cyanobiphenyl-4yl)ethane
1-(2-fluoro-4-n-propylphenyl)-2-(4'-trifluoromethylbiphenyl-4-yl)ethane
1-(2-fluoro-4-n-pentylphenyl)-2-(4'-trifluoromethylbiphenyl-4-yl)ethane
1-(2-fluoro-4-n-propylphenyl)-2-(4'-trifluoromethoxybiphenyl-4-yl)ethane
1-(2-fluoro-4-n-pentylphenyl)-2-(4'-trifluoromethoxybiphenyl-4-yl)ethane
1-(2-fluoro-4-n-propylphenyl)-2-(4'-difluoromethoxybiphenyl-4-yl)ethane
1-(2-fluoro-4-n-pentylphenyl)-2-(4'-difluoromethoxybiphenyl-4-yl)ethane
1-(p-n-propylphenyl)-2-(4'-trifluoromethyl-2'-fluorobiphenyl-4-yl)ethane
1-(p-n-propylphenyl)-2-(4'-trifluoromethoxy-2'-fluorobiphenyl-4-yl)ethane
1-(p-n-propylphenyl)-2-(2',4'-difluorobiphenyl-4-yl)ethane

We claim:

1. A nematic liquid crystalline phase containing at least two liquid crystalline components, characterized in that it contains at least one compound of Formula I

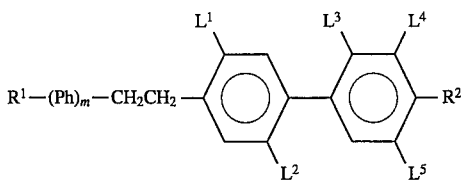

in which one of the radicals $R^1$ and $R^2$ is X and the other radical $R^1$ or $R^2$ is R—Y—
where
X is halogen, —OCHF$_2$ or OCF$_3$,
is alkyl, fluoroalkyl, or oxaalkyl radicals of up to 10 C atoms and
Y is O, S, —CO—O—, —O—CO—, —O—CO—O—, a single bond or—in the case where m=1—alternatively trans-1,4-cyclohexylene or

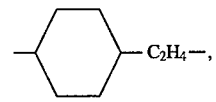

m is 1 or 2,
Ph is in each case identical or different radicals selected from the group comprising 1,4-phenylene, 2-fluoro-1,4-phenylene, 3-fluoro-1,4-phenylene and 3,5-difluoro-1,4-phenylene,
$L^3$ and $L^4$ are each H, or one of these radicals is alternatively F, and
$L^1$, $L^2$
and $L^5$ are each H or F.

2. Liquid-crystal display element, characterized in that it contains a nematic liquid-crystalline phase according to claim 1.

3. A method of using a nematic liquid crystalline phase according to claim 1 with compounds of Formula I

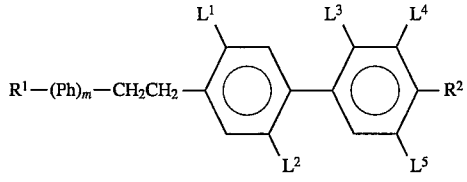

in which one of the radicals $R^1$ and $R^2$ is X and the other radical $R^1$ or $R^2$ is R—Y—
where
X is halogen, —OCHF$_2$, or —OCF$_3$,
R is alkyl, fluoroalkyl, or oxaalkyl radicals of up to 10 C atoms and
Y is O, S, —CO—O—, —O—CO—, —O—CO—O—, a single bond or—in the case where m=1—alternatively trans-1,4-cyclohexylene or
m is 1or 2,
Ph is in each case identical or different radicals selected from the group comprising 1,4-phenylene, 2-fluoro-1,4-phenylene, 3-fluoro-1,4-phenylene and 3,5-difluoro-1,4-phenylene,
$L^3$ and $L^4$ are each H, or one of these radicals is alternatively F, and
$L^1$, $L^2$
and $L^5$ are each H or F,
said method comprising incorporating said nematic liquid crystal phase in a liquid crystal display element and operating said liquid crystal display element.

4. A nematic phase according to claim 1, wherein R is straight-chain alkyl of 2 to 7 C atoms.

5. A nematic phase according to claim 1, wherein R is oxaalkyl.

6. A nematic phase according to claim 5, wherein oxaalkyl is ethoxy, propoxy, butoxy, pentoxy, hexoxy, heptoxy, 2-oxapropyl (=methoxymethyl), 2-(=ethoxymethyl) or 3-oxabutyl (=2-methoxyethyl), 2-, 3- or 4-oxapentyl, 2-, 3-, 4- or 5-oxahexyl, 2-, 3-, 4-, 5- or 6-oxaheptyl.

7. A nematic phase according to claim 1, wherein m is 1.

8. A nematic phase according to claim 1, wherein Y is trans-1,4-cyclohexylene, —O—, or a single bond.

9. A phase according to claim 1, wherein the lateral substitution pattern for the compound of formula I, is as follows:

| $L^1$ | $L^2$ | $L^3$ | $L^4$ | $L^5$ |
|---|---|---|---|---|
| H | F | H | H | H |
| H | H | H | F | H |
| H | H | H | F | F |
| H | F | H | F | H |
| H | F | H | F | H. |

10. A nematic liquid crystalline phase comprising at least two liquid crystalline components, which contains at least one compound of the formula Ia

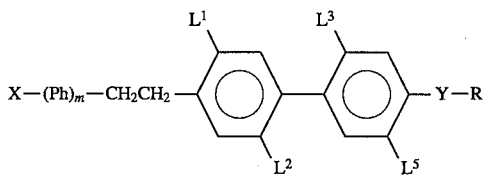

in which

R is alkyl, fluoroalkyl, or oxaalkyl radicals of up to 10 C atoms;

m is 1 or 2;

Y is O, S, CO—O—, O—CO, O—CO—O, a single bond, or, in the case where m is 1, alternatively trans-1,4-cyclohexylene;

Ph is in each case identical or different radicals selected from the group comprising 1,4-phenylene; 2-fluoro-1,4-phenylene; 3-fluoro-1,4-phenylene; and 3,5-difluoro-1,4-phenylene;

$L^1$, $L^2$, $L^3$, and $L^5$ are each H or F; and

X is F, Cl, —OCF$_3$, or —OCHF$_2$.

11. A nematic phase according to claim 10, wherein the lateral substitution pattern for the compounds of formula Ia is as follows:

| $L^1$ | $L^2$ | $L^3$ | $[L^4]$ | $L^5$ |
|---|---|---|---|---|
| H | H | F | [H] | H |
| F | H | H | [H] | H |
| F | H | F | [H] | H. |

12. A nematic phase according to claim 10, which contains at least one of the following compounds:

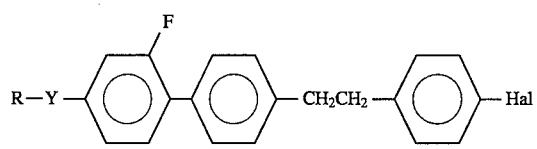

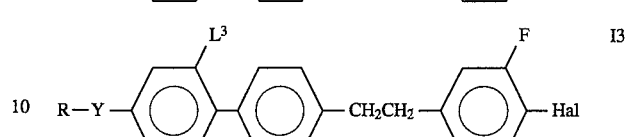

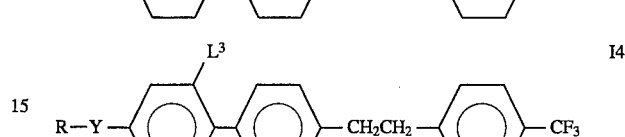

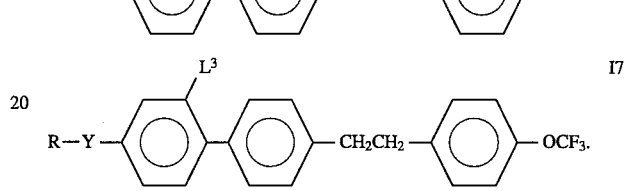

13. A nematic phase according to claim 10, which contains at least one of the following compounds:

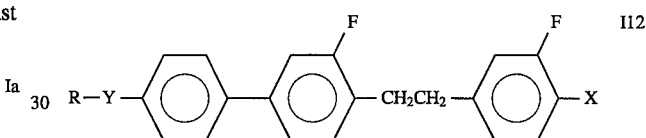

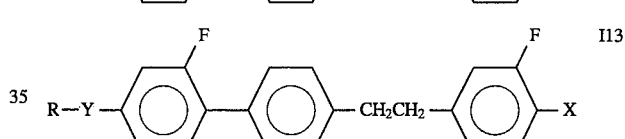

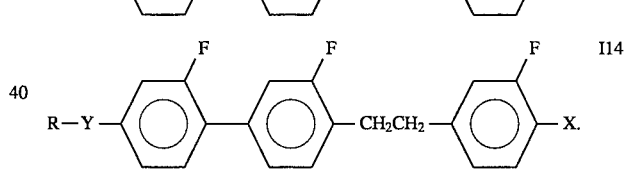

14. Liquid-crystal display element, characterized in that it contains a nematic liquid-crystalline phase according to claim 10.

15. A phase according to claim 10, wherein R is straight-chain alkyl of 2 to 7 C atoms.

16. A phase according to claim 10, wherein R is oxaalkyl.

17. A phase according to claim 16, wherein oxaalkyl is ethoxy, propoxy, butoxy, pentoxy, hexoxy, heptoxy, 2-oxapropyl(=methoxymethyl), 2-(=ethoxymethyl) or 3-oxabutyl (=2-methoxyethyl), 2-, 3- or 4-oxapentyl, 2-, 3-, 4- or 5-oxahexyl, 2-, 3-, 4-, 5- or 6-oxaheptyl.

18. A phase according to claim 10, wherein m is 1.

19. A phase according to claim 10, wherein Y is trans-1,4-cyclohexylene, —O—, or a single bond.

20. A nematic liquid crystalline phase comprising at least two liquid crystalline components, which contains at least one compound of the formula Ib

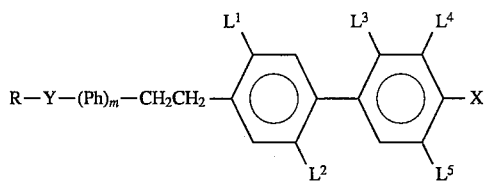
Ib in which
- R is alkyl, fluoroalkyl, or oxaalkyl radicals of up to 10 C atoms;
- m is 1 or 2;
- Y is O, S, CO—O—, O—CO, O—CO—O, a single bond, or, in the case where m is 1, alternatively, trans-1,4-cyclohexylene;
- Ph is in each case identical or different radicals selected from the group comprising 1,4-phenylene; 2-fluoro-1,4-phenylene; 3-fluoro-1,4-phenylene; and 3,5-difluoro-1,4-phenylene;
- $L^1$, $L^3$, and $L^4$ are each H, or one of these radicals is alternatively F;
- $L^2$ and $L^5$ are each H or F; and
- X is halogen, —$CF_3$, or —$OCF_3$, with the proviso that in the case where X is halogen or —$CF_3$, Y is trans-1,4-cyclohexylene or m is 2 or $L^4$ and/or $L^5$ is fluorine.

21. A nematic phase according to claim 20, wherein the lateral substitution pattern for the compound of formula Ib is as follows:

| $L^1$ | $L^2$ | $L^3$ | $L^4$ | $L^5$ |
|---|---|---|---|---|
| H | F | H | H | H |
| H | H | H | F | H |
| H | H | H | F | F |
| H | F | H | F | H |
| H | F | H | F | H. |

22. A nematic phase according to claim 20, which contains at least one of the following compounds:

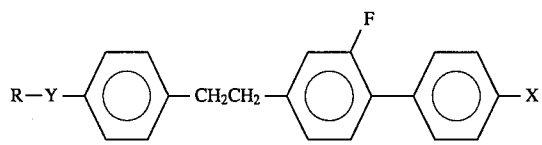
I18

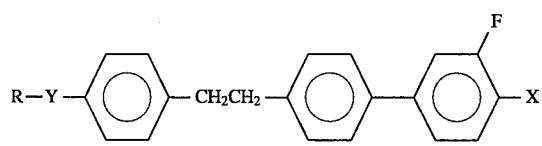
I21

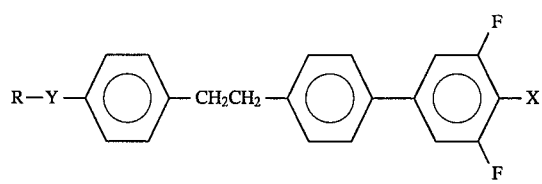
I22

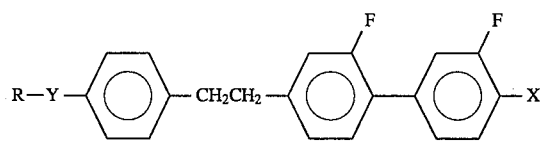
I29

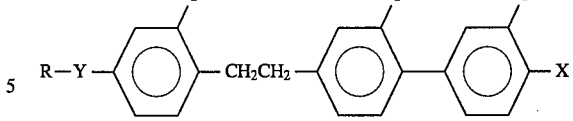
I30

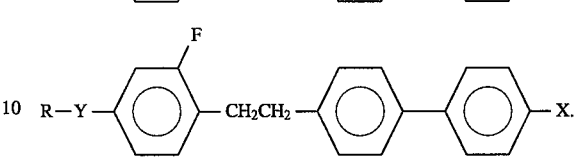
I36

23. A nematic phase according to claim 20, which contains at least one of the following compounds:

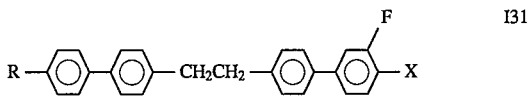
I31

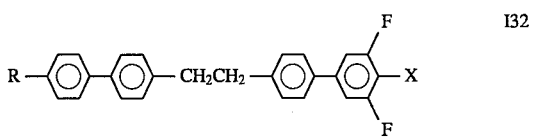
I32

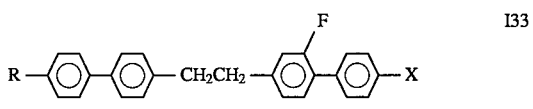
I33

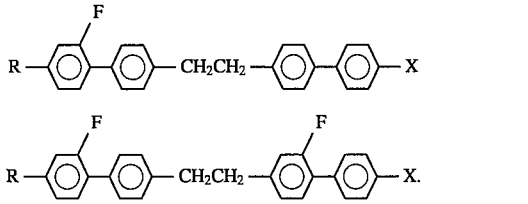

24. A nematic phase according to claim 20, which contains at least one of the following compounds:

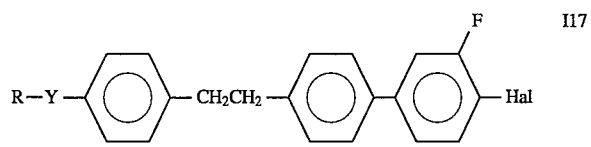
I17

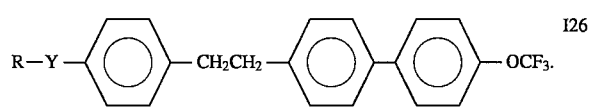
I26

25. A nematic phase according to claim 20, which contains at least one compound of the formula V:

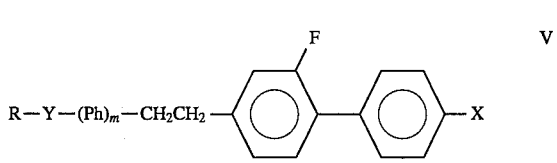
V

26. Liquid-crystal display element, characterized in that it contains a nematic liquid-crystalline phase according to claim 20.

27. A phase according to claim 20, wherein R is straight-chain alkyl of 2 to 7 C atoms.

28. A phase according to claim 20, wherein R is oxaalkyl.

29. A phase according to claim 28, wherein oxaalkyl is ethoxy, propoxy, butoxy, pentoxy, hexoxy, heptoxy, 2-oxapropyl(=methoxymethyl), 2-(=ethoxymethyl) or 3-oxabutyl (=2-methoxyethyl), 2-, 3- or 4-oxapentyl, 2-, 3-, 4- or 5-oxahexyl, 2-, 3-, 4-, 5- or 6-oxaheptyl.

30. A phase according to claim 20, wherein m is 1.

31. A phase according to claim 20, wherein Y is trans-1,4-cyclohexylene, —O—, or a single bond.

* * * * *